US008021435B2

(12) United States Patent
Bravo Castillo

(10) Patent No.: US 8,021,435 B2
(45) Date of Patent: Sep. 20, 2011

(54) FUNCTIONAL HAND PROSTHESIS MECHANISM

(76) Inventor: Luis Armando Bravo Castillo, Tlalnepantla de Baz (MX)

( * ) Notice: Subject to any disclaimer, the term of this patent is extended or adjusted under 35 U.S.C. 154(b) by 0 days.

(21) Appl. No.: 12/523,643

(22) PCT Filed: Dec. 4, 2007

(86) PCT No.: PCT/MX2007/000148
§ 371 (c)(1),
(2), (4) Date: Feb. 18, 2010

(87) PCT Pub. No.: WO2008/088204
PCT Pub. Date: Jul. 24, 2008

(65) Prior Publication Data
US 2010/0217405 A1    Aug. 26, 2010

(30) Foreign Application Priority Data

Jan. 17, 2007    (MX) .................. MX/A/2007/000682

(51) Int. Cl.
*A61F 2/54* (2006.01)
(52) U.S. Cl. .......................................... 623/64; 901/39

(58) Field of Classification Search .................. 294/106, 294/115; 901/39; 623/61, 64
See application file for complete search history.

(56) References Cited

U.S. PATENT DOCUMENTS

| 3,202,449 | A | * | 8/1965 | Lemelson | 294/88 |
| 3,822,418 | A | | 7/1974 | Yakobson et al. | |
| 4,094,016 | A | | 6/1978 | Eroyan | |
| 4,149,278 | A | * | 4/1979 | Frosch et al. | 623/62 |
| 4,600,357 | A | * | 7/1986 | Coules | 414/730 |
| 4,921,293 | A | | 5/1990 | Ruoff et al. | |
| 5,062,673 | A | | 11/1991 | Mimura | |
| 5,108,140 | A | * | 4/1992 | Bartholet | 294/106 |
| 5,326,369 | A | * | 7/1994 | Schectman | 623/24 |
| 6,921,419 | B2 | * | 7/2005 | Weir et al. | 623/64 |

* cited by examiner

*Primary Examiner* — Bruce E Snow
(74) *Attorney, Agent, or Firm* — Feldman Gale, P.A.; Walter C. Frank

(57) ABSTRACT

A functional prosthesis for a hand comprises an opening and closing mechanism for articulated fingers. A worm gear coupled to a DC actuator-motor provides linear movement to a displacement mobile which is coupled to articulated fingers of the artificial hand. When the actuator rotates in one direction, the displacement mobile moves in one direction, causing the fingers to open or close, depending upon the direction of rotation. Rotation of the actuator in the opposite direction will cause the fingers to move in the opposite direction.

12 Claims, 6 Drawing Sheets

FUNCTIONAL HAND PROSTHESIS MECHANISM

CROSS REFERENCE TO RELATED APPLICATIONS

This application is the United States National Phase of International Application No. PCT/MX2007/000148, filed Dec. 4, 2007 which claims priority under 35 U.S.C. 119(a-d) to Mexican Application No. MX/a/2007/000682.

FIELD OF THE INVENTION

The present invention is in the field of the prosthetic devices. It particularly refers to a functional prosthesis for the human hand, and offers anyone with an amputation a different rehabilitation option by using a practical, efficient and innovative technology.

For quite some time, the need to develop apparatus or systems to help those who have lost an upper or lower limb either due to an accident or a malformation from birth, has led to the exploration and development of prostheses in this capacity. As a result of the development of a functional prosthesis, the population who suffered an amputation is offered an option for their rehabilitation which employs the technological developments that have been generated in this invention.

BACKGROUND OF THE INVENTION

The first prostheses had a merely esthetical function meaning that they were not functional. Thereafter, mechanical prostheses were developed. Still later, the upper limb (arm) prosthesis, which is operated by a whip that follows the movements of the shoulder, came to be substituted for the traditional mechanical clamp or hook prosthesis. Today there are functional prostheses with a higher technological development which allows them to be ergonomic, easily operated, and having better aesthetics, coming closer to the appearance and functioning of a real leg or arm.

Based on research, we have found several technologies which apply different mechanisms that focus on the field of the upper limb prostheses, particularly those for the hand. From these technologies, we shall list the ones having a closer technical resemblance to the functional mechanism for a functional prosthesis for a hand.

U.S. Pat. No. 5,013,326 ("U.S. '326 patent") describes a hand provided with turned fingers of a certain curvature, their axis being at a 30° angle with respect to the angle of the forearm. This device is able to grab elements or lift small objects located on a surface. The movement of the turned phalanges is transmitted by means of an internal rack.

Japanese Patent 2,080,044 ("JP '044") bases its operation on a mechanism which is very similar to the one described in the U.S. '326 patent. The mechanical system in JP '044 corresponds to 3 hooks located in such manner that they simulate the thumb, index and middle fingers. It approaches part of its description on the actuator that generates the movement of the hand.

Document WO 0069375, 1968 ("WO '375") discloses a hand prosthesis which has an individual movement in each of its five fingers, each finger having an independent actuator whose movement is controlled by means of extensometric calipers.

U.S. Pat. No. 5,200,679, 1993 ("U.S. '679 patent") describes a robotic hand which uses a prosthetics element which includes 5 fingers. It has a dual action motor that uses two cables to generate the opening and closing movements of the hand. When the motor turns in one direction, it generates tension on the first cable, which causes the phalanges to retract toward the palm of the hand, generating the closing movement. Afterwards, tension is generated on the second cable, due to the inverse turn of the motor, that causes the fingers to return to the original extension position which is the opening of the hand.

U.S. Pat. No. 4,114,464 ("U.S. '464") deals with an artificial hand mechanism which has at least one finger and a thumb which generate together the opening and closing movement of the hand by means of a gear joined to each one of them. At the same time, they are adjusted to a screw tip gear that is coupled to a motor.

U.S. Pat. No. 4,377,305 ("the '305 patent") describes the functioning of an artificial hand which has two fasteners which articulate on a bolt that provides them with the opening and closing movement of the fasteners, and also provides them with a flexion-extension movement over the same quadrant or plane as the opening and closing movement. The fasteners can rotate since they are assembled on an axis parallel to the axis of the bolt. The opening and closing movement of the fasteners is done by means of a curve section dual rack and a straight gear mechanically coupled to them. It also has an adduction and abduction movement as well as a wrist turn.

U.S. Pat. No. 5,080,681, 1990 ("U.S. '681") describes the functioning of an artificial hand that consists of two mobile phalanges and a hook that simulates the thumb. The closing and opening movement of the phalanges described in this prosthetic mechanism is provided by means of a mobile mechanism activated by an actuator. When activated, the mobile device glides through a guide which is located on the chassis of the artificial hand. It has a system of artificial tendons which are joined to the mobile device on one side and then to the phalanges. When the device moves towards proximal (the patient's body), the tendons contract and generate the closing movement of the fingers and when the device moves towards distal, the tendons relax and generate the opening movement of the fingers.

U.S. Pat. No. 5,888,246 ("U.S. '246") describes the coupling between a worm gear and a round gear joined to a finger member. The worm gear transmits the movement to the round gear which generates the angular movement of a member simulating a finger. This coupling may be coupled to an artificial hand.

U.S. Pat. No. 5,378,033 ("U.S. '033") describes a complex hand mechanism which consists of three fingers assembled on a pair of plates which are toothed in three sections of their periphery. The hand may be turned by means of gears which transmit the movement coming from a motor. Opening and closing movements are given by means of a mechanism which has two conical gears joined, one to the axis of the motor and the other to a cam with a follower that is joined to three elements that serve as a guide for the base of the fingers. The maximum elevation trajectory of the follower generates a movement to the three guides joined to each finger. They, in turn, transmit the displacement movement to the base of the fingers that articulate in one of the disks, thus generating a lever effect with which they open. This movement is transmitted to the phalanges by means of a system of gears coupled from the base of the finger to the distal phalanx of the finger on both sides of the finger. When the follower moves upward, the fingers open; when the follower descends, the fingers close.

Document GB 2072020 ("GB '020") describes the functioning of a hand prosthesis that uses a standard worm gear for the opening and closing action of the fingers. This particular hand prosthesis is similar to the invention except that the movement of the finger, the placement of the motor, the type of impeller screw, and the coupling of the motor to the worm gear are different in the present invention from those disclosed in GB '020.

Document CN 2680418Y ("CN '18Y") describes the functioning of an artificial hand using the worm gear system aided by a lever or rod to move the thumb.

Among the disclosures described herein, and others existing in the field, there are some hand prostheses which control the function of fingers opening and closing using a worm gear with a standard chord. The present invention is an improvement over such other prostheses in that not only the drive system of the fingers of the present invention, but also the plate that supports the elements, provide a functionality of the fingers and hand that is not found in prior art embodiments.

SUMMARY OF THE INVENTION

The mechanism for a functional prosthesis for a hand includes a support plate 5 having a 'U' shape with a hole through the central part of the curvature at the proximal end that supports an actuator which is, preferably, a DC motor. The internal walls of the support plate have a pair of guides 5b that support a safety plate 10. A second pair of displacement guides 5a receive a displacement mobile 8 which glides with a linear movement along the guides. As shown in FIGS. 8 and 9, movement of the mobile within the displacement guides is controlled by a worm gear 9 having four channels 9a. The worm gear joins the actuator shaft of a DC motor 13 at its proximal end 14. At the distal end of the support plate 5, three fingers are assembled and articulated. The prosthesis also has an artificial wrist 16 located near the proximal end of the support plate 5 where part of the actuator body of the DC motor is located 13. A join plate 11 joins support plate 5 with the artificial wrist 16.

DETAILED DESCRIPTION OF THE INVENTION

Figure 1:
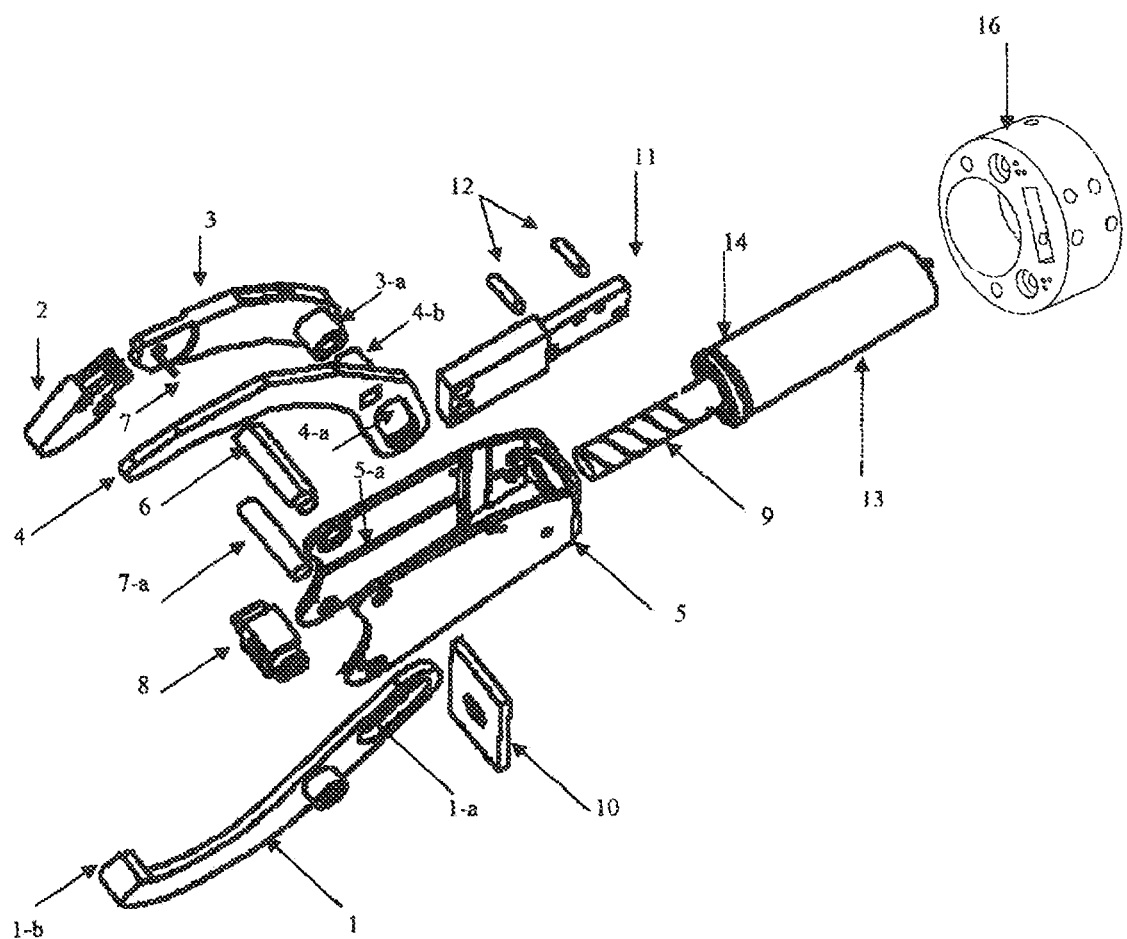
FIG. 1 is an exploded perspective view of the mechanism for a functional prosthesis for a hand.

The mechanism for a functional prosthesis for a hand consists of an artificial hand module with opening and closing movements. This action is generated by means of a worm gear system 9 and a displacement mobile 8. The prosthesis can be manufactured preferably in aluminum, nylon, carbon fiber, stainless steel and bronze.

The functional prosthesis mechanism for a hand has a support plate 5 which may be made of a light and highly resistant material such as alumec 89. The support plate is formed generally into a "U" having opposite sidewalls and a rear wall. The special feature of this support plate is that it has displacement guides machined into the internal side of its opposing sidewalls, 5-a, shown in FIG. 7, parallel to the actuator's rotor axis 13. In the preferred embodiment, a direct current (DC) motor is used, which permits the guide pins 8c of the displacement mobile 8, shown in FIG. 9, to glide in a linear movement within the sidewalls of the support plate 5 to generate the action of opening and closing of the fingers. Each sidewall of the support plate 5 also has a channel guide 5b machined in a direction perpendicular to the actuator's rotor axis, which serves to hold the safety plate 10, and which prevents the actuator's shaft 13 from coming out of the actuator's casing when a very high pressure is placed upon it as a result of lifting elements of considerable weight.

The support plate also has holes in its sidewalls to accept the shafts 6 and 7a in FIG. 1, over which the fingers are articulated. In the preferred embodiment, the holes are drilled although they may also be created by other means. A hole is also formed in the rear wall where the actuator, 13 extends through the support plate 5 and is fastened or coupled to the support plate by means of fastening elements, such as stud bolts, rivets, or other suitable attachment means.

To provide more safety and functionality to the system, an artificial wrist 16 is located near the proximal part (rear wall) of the support plate 5. The wrist 16 has a cavity for the actuator 13 and a slot 16a where an end of the join plate 11 is secured. The join plate 11 secures the artificial wrist with a joint plate by means of fastening elements. In this manner, it provides support and linkage to the actuator 13. The artificial wrist may also have holes to receive bolts or other fasteners to attach the wrist to a mechanical element or a user's forearm extension.

Figure 2:
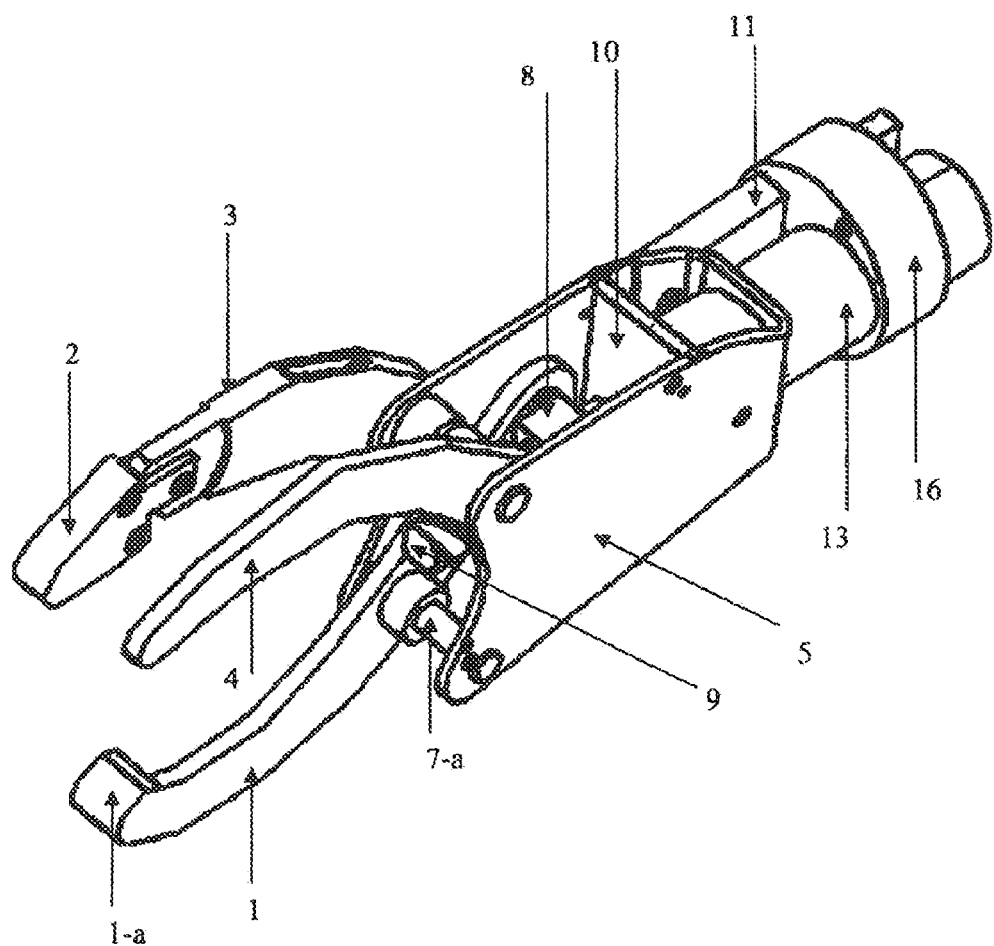
FIG. 2 is a perspective view joining the elements described on FIG. 1.
Figure 3:
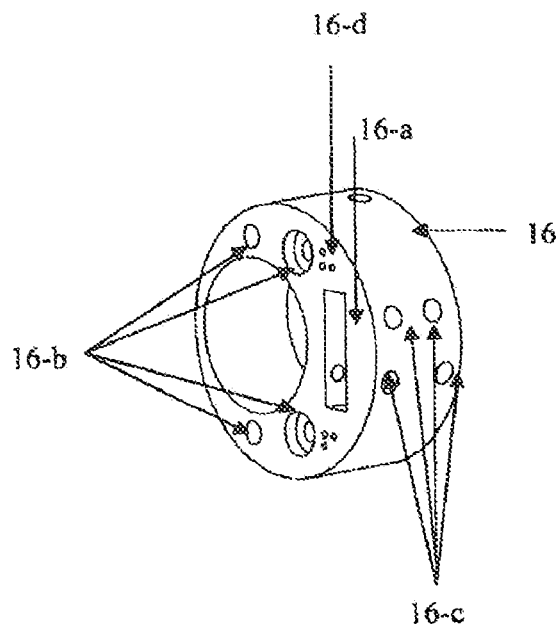
FIG. 3 is a perspective view of the artificial wrist.

The artificial hand mechanism has three fingers. The thumb 1 with its toe 1-b provides a large contact surface. An opposing index finger includes an articulated distal phalange 2 and an index finger body 3. A middle finger 4 also opposes the thumb. These elements are attached to the distal end of the support plate 5 and are articulated and supported on the support plate using bolts 6 and 7a. The articulated distal phalange 2, the index finger body 3, the middle finger 4 and the thumb 1 are assembled on the support plate 5, as shown in FIG. 2.

Figure 5:
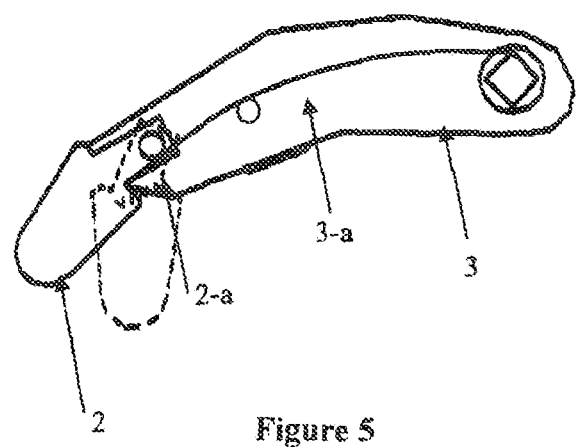
FIG. 5 is a perspective view showing the detail of the index finger and the spring and the tensor.
Figure 6:
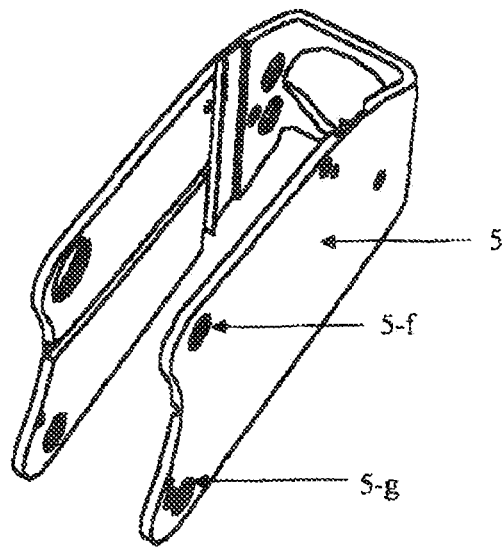
FIG. 6 is a perspective view of the support plate for the hand's elements.
Figure 7:
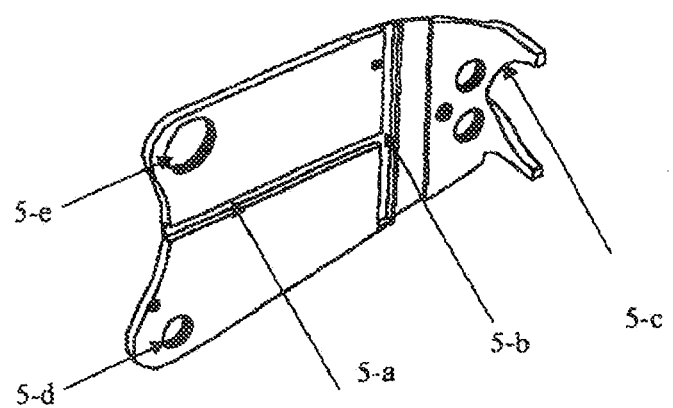
FIG. 7 is a partial perspective view of the longitudinal section of the support plate.

The articulated distal phalange element 2 is articulated on the index finger body 3 by means of a bolt or pin 7. As shown in FIGS. 5 and 7, hollow pin 3a fits into hole 5e located on the support plate 5. The middle finger 4 transmits its movement to index finger body 3 by means of a bolt or pin 6. In the preferred embodiment, a rectangular bolt 6 is used, which enters into pins 3a and 4b. FIG. 1 shows bolt 6 having a cylindrical element at one end which is inserted into hole 5f in FIG. 6, and is secured by a fastening element (not shown). Thumb 1 is articulated by means of a bolt 7a which is secured in holes 5d and 5g. Finger 1 is attached to bolt 7a by a fastening element (not shown).

Thumb 1 is opposed to the two remaining digits and their opening and closing movement is carried out by means of the stress between the worm gear 9 and the pins of the displacement mobile 8. The movement is transmitted by an actuator 13 which, in the preferred embodiment, is a DC motor.

Figure 4:
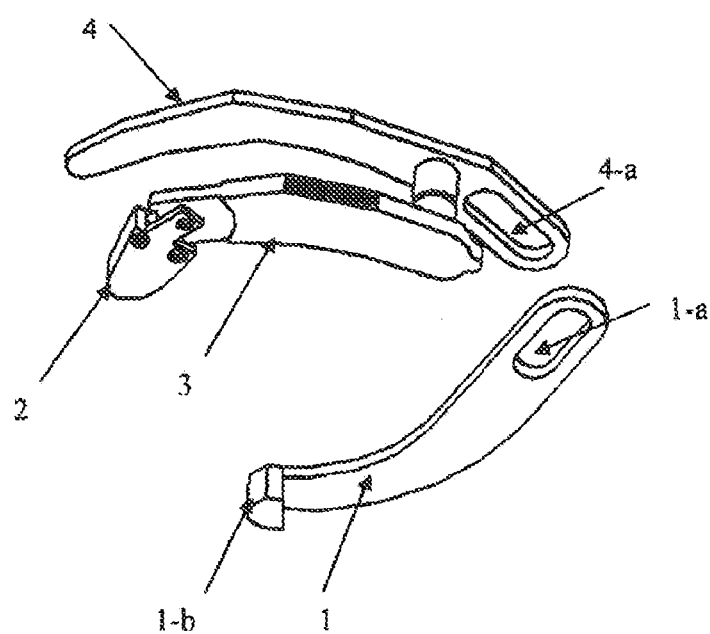
FIG. 4 is an exploded view of the system's fingers.

Fingers 1 and 4 have gliding guides, 1a and 4a, respectively, depicted in FIG. 4, which are guided by guide pins 8c as the displacement mobile 8 moves. These guides permit an angular displacement of the fingers by the linear movement of the displacement mobile 8, which moves along the worm gear 9 that is mechanically joined to the actuator shaft 13.

Figure 8:
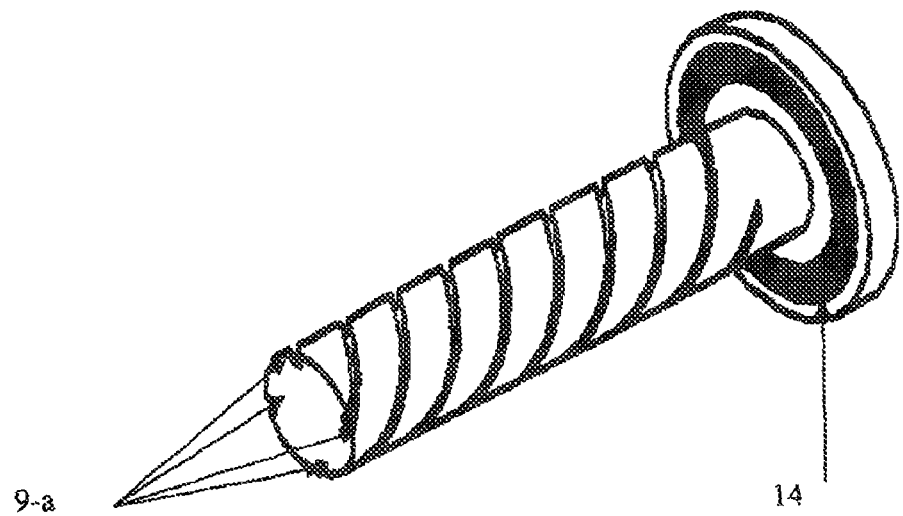
FIG. 8 is a perspective view of the worm gear with four channels and a bearing.
Figure 9:
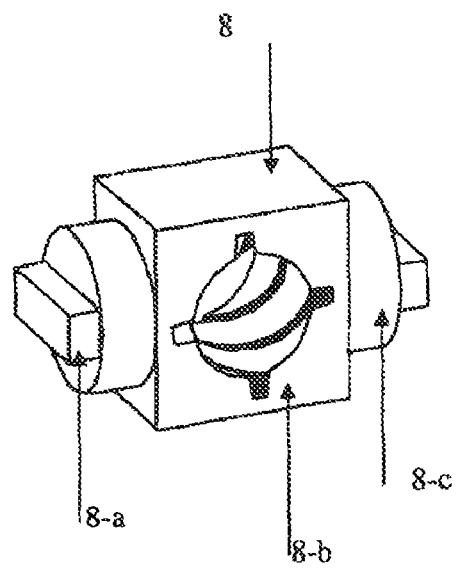
FIG. 9 is a perspective view of the displacement mobile.

In FIGS. 8 and 9, the displacement mobile 8 is shown to have four channels 8*b* which are threaded onto worm gear 9. Projecting tongues 8*a* glide within guide channels 5*a* and its corresponding opposite channel machined into the opposite face of support plate 5. These channels permit displacement mobile 8 to glide within support plate 5 while maintaining a completely linear displacement.

In the preferred embodiment, worm gear 9 has a safety plate 10 which is located on the support plate 5, and that prevents worm gear 9 from gliding or have a clearance over support plate 5. Safety plate 10 also provides safety to actuator shaft 13 when the patient lifts elements of considerable weight. As shown in FIG. 6, guides 5*b* are machined into opposite sides of support plate 5 within which the safety plate 10 may be adjusted. These guides provide a limit for the plate, thus preventing safety plate 10 from being displaced or having undesired movement with respect to support plate 5. A bearing 14 is located adjacent to actuator shaft 13 to provide a means for adjustment and to prevent prevents the friction between worm gear 9 and safety plate 10.

The speed with which the fingers open and close depends upon the relationship between the number of screw gear channels and the diametric pitch of those channels. However, other embodiments may have a greater or lesser number of channels, depending on the needs of the system.

In the patent documents GB '020 and CN '18Y, a worm gear is disclosed as a drive system for opening and closing the fingers. These devices use a standard chord for the worm gear, in contrast to the one used in the present invention. The problem with the devices shown in GB '020 and CN '18Y is that the speed with which the fingers may be opened or closed is dependent upon energy consumption of the device; that is, a higher consumption of energy is required by the actuators in order to accelerate the opening or closing of the fingers. At the same time, a higher operating speed reduces the torque or power available from the DC motor, and would be manifested by the fingers having too little strength to lift elements with a considerable weight. On the other hand, if a larger torque is required, the speed with which the fingers open and close would be considerably reduced.

The problem of opening and closing speed is solved with the worm gear disclosed in the present invention, which is not a standard gear, but in the preferred embodiment has four channels which allows a forward movement of between 4 and 5 times greater than would be possible with conventional gears. This allows the worm gear of the invention to have considerable speed and an elevated torque without having higher current consumption. By using a four channel screw 9*a*, a good finger opening and closing speed and a high torque are obtained, and neither speed nor strength, which are extremely important for a hand prosthesis, are sacrificed, and a higher electric power consumption is not encountered.

In the present invention, there is a relation between the number of screw channels which control the forward movement, and the speed with which the displacement mobile moves over the worm gear. These parameters may be adjusted depending on the patient's needs.

The operation manner of this set of elements is as follows: When the actuator 13 is energized with a positive-negative polarity, its shaft transmits its rotational movement to the worm gear 9. Since they are mechanically coupled, the rotational action of the worm gear causes the displacement mobile 8 have a linear displacement, parallel to the actuator's rotor axis 13, form proximal to distal. This displacement causes the fingers 1 and 4 to have an angular movement which generates the opening and closing action of the fingers. Finger movement is controlled by the guide pins 8*c* of the mobile 8 by means of the gliding guides 1*a* and 4*a* respectively. As displacement mobile 8 moved linearly in a distal direction, fingers 1 and 4 are given an angular movement which generates the opening action of the fingers.

Figure 10:
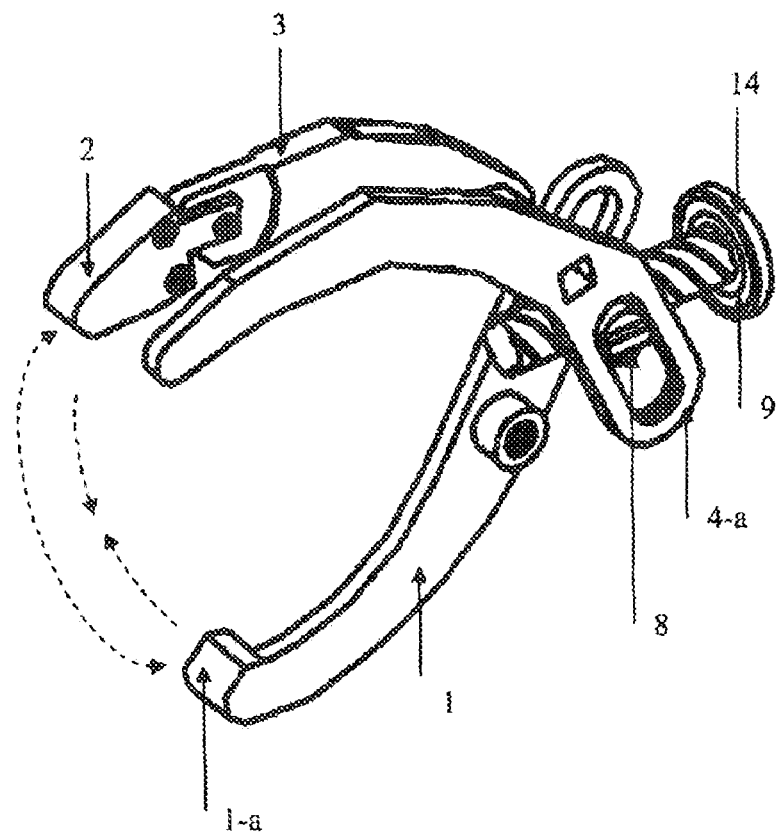
FIG. 10 shows the placement and connection of the finger's coupling with the worm gear and displacement mobile.
Figure 11:
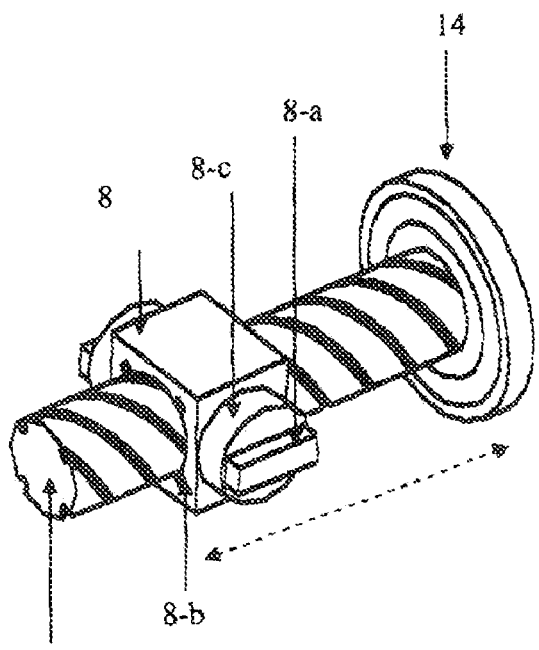
FIG. 11 depicts the displacement mobile coupling with the worm gear.

To close the fingers, the functioning is the same, but in the opposite direction. The actuator must be polarized or energized in an inverse manner, which generates a displacement of the mobile 8 from distal to proximal along the displacement guides 5*a*. In FIG. 10 the opening and closing movement of the fingers is depicted, along with the coupling of the fingers over the guide pins 8*c* of the displacement mobile 8 and the mobile's threaded connection to the worm gear 9.

The system is provided with electromechanical switches which prevent the opening and closing system of the fingers to continue operating after reaching the maximum opening and closing limits. When the maximum operational limits are reached, the current that is sent to the actuator is shut off.

When the closing movement of the fingers occurs, the movement of the articulated phalange 2 is generated over index finger body 3. This mechanism works in the following way: the articulated phalange 2 maintains an original position (of extension) when the hand is open by means of a resistive element or spring 2*a* located between phalange 2 and index finger body 3, as shown in FIG. 4. When the hand closes, there is an internal tensor element 3*b* in the index finger body 3 that causes phalange 2 to retract toward the internal part of the hand, breaking the strength of the spring 2*a*. Retraction of phalange 2 is caused by pressing it in such a way that, when the finger reaches its maximum closing position, toe 1*b* of thumb 1 contacts the articulated phalange 2. This contact allows the patient to grasp small elements between the toe 1*b* and phalange 2 with higher precision and control.

When the hand opens, the spring 2*a* that is under compression operates again causing phalange 2 to return to its original position and the tensor 3*b* is at rest. With this movement, the artificial hand has a closer resemblance to a natural one. Unlike natural hands, artificial hands already in the market have a thumb that is longer than a human thumb. However, the prosthesis of this invention provides a more natural movement, as described, and provides the patient with greater ability to use the hand in a natural manner. The dimensions of the mechanism for a functional prosthesis mechanism for a hand, within its mechanical elements, are subjected to the patient's anatomy and may be varied in order to provide the patient with a prosthesis that largely mimics the natural movements of a human hand.

When the hand opens, the spring 2*a* that is under compression operates again causing phalange 2 to return to its original position and the tensor 3*b* is at rest. With this movement, the artificial hand has a closer resemblance to a natural one. Unlike natural hands, artificial hands already in the market have a thumb that is longer than a human thumb. However, the prosthesis of this invention provides a more natural movement, as described, and provides the patient with greater ability to use the hand in a natural manner. The dimensions of the mechanism for a functional prosthesis for a hand, within its mechanical elements, are subjected to the patient's anatomy and may be varied in order to provide the patient with a prosthesis that largely mimics the natural movements of a human hand.

I claim:

1. A functional prosthesis mechanism for a hand comprising:
   a support plate, a displacement mobile, an actuator, and a safety plate,
   a worm gear having a plurality of channels,
   three fingers,
   a wrist,
   a join plate,
   said support plate comprising an opening to receive said actuator, a pair of displacement guides for supporting said displacement mobile, and a pair of perpendicular guides for holding said safety plate;
   said displacement guides providing support for said displacement mobile while allowing linear movement of said displacement mobile within said support plate;
   said actuator comprising a body and a shaft;
   said displacement mobile having internal threads to receive said worm gear and being moved linearly upon rotation of said worm gear, and a pair of guide pins;
   said worm gear being joined to said actuator shaft at a proximal end of said worm gear;
   said three fingers being assembled and articulated at the distal end of said support plate, at least two of said fingers having guide slots to receive said guide pins of said displacement mobile;
   said artificial wrist being located at a proximal end of said support plate, said artificial wrist supporting part of said actuator body and having a cavity to receive said joint plate;
   whereby, upon activation of said activator, said worm gear will rotate to produce linear movement of said displacement mobile, said movement causing said articulated fingers to open or close, depending upon the direction of rotation of said worm gear.

2. The functional prosthesis mechanism for a hand as claimed in claim 1, said join plate being fastened to said wrist at one end of said join plate, and being fastened to said support plate at said opposite end, said actuator further comprising a DC motor, whereby said safety plate works together with said wrist to avoid longitudinal movement of said actuator.

3. The functional prosthesis mechanism for a hand as claimed in claim 2, said three fingers further comprising a thumb, an index finger, and a middle finger;
   said thumb having a toe, said toe having a contact surface for grasping items that can be picked up;
   said index finger comprising an articulated distal phalange and an index body;
   said fingers being assembled on said distal end of said support plate and being articulated around shafts located on said support plate.

4. The functional prosthesis mechanism for a hand as claimed in claim 3, said index finger further comprising an articulated distal phalange that is articulated on a shaft such that, when said linear movement of said displacement mobile causes a closing movement of said fingers, an internal tensor causes said articulated distal phalange to contract toward the inner part of the hand, pressing a spring, and meeting said toe of said thumb, whereby small or slim elements may be grasped; and when said linear movement of said displacement mobile causes an opening movement of said fingers, said distal phalange of said index finger and said toe of said thumb work inversely, releasing grasping pressure on an object located between said distal phalange and said toe.

5. The functional prosthesis mechanism for a hand as claimed in claim 4, further comprising said guide pins extending through guide slots in said thumb and middle fingers, said guide pins gliding in a straight line along said displacement guides of said support plate, said guide slots being coupled in a rotary manner over said guide pins, whereby longitudinal displacement of said displacement mobile causes said fingers to open or close depending on the turn of the actuator and the rotational direction of said worm gear.

6. The functional prosthesis mechanism for a hand as claimed in claim 5, further comprising said channels on said worm gear being coupled to said internal threads of said displacement mobile, causing said displacement mobile to glide longitudinally along said displacement guides when said worm gear rotates.

7. The functional prosthesis mechanism for a hand as claimed in claim 6, said artificial wrist further comprising a hole to receive said actuator and fastening means to secure said actuator to said wrist, said wrist further comprising a slot dimensioned to couple and secure said wrist to said join plate, said wrist also further comprising attachment means to attach said wrist to a mechanical element or a forearm extension.

8. The functional prosthesis mechanism for a hand as claimed in claim 7, further comprising said middle finger transmitting its movement to said index finger through a shaft having at least one flat side along part of its length, one end of said shaft fitting into a round hole on one side of said support plate and extending through a non-circular hole in said middle finger, the opposite end of said shaft being received in a non-circular receptacle on said index finger, such that rotation of said shaft causes said index finger and said middle finger to rotate together.

9. The functional prosthesis mechanism for a hand as claimed in claim 8, further comprising said middle finger being located adjacent an interior side of a first sidewall of said support plate; said index finger being located adjacent an external side of a second sidewall; and said thumb being located adjacent an interior side of said second sidewall.

10. The functional prosthesis mechanism for a hand as claimed in claim 9, said thumb further comprising a length which is proportional to that which a biological hand has in comparison with a biological index finger of the biological hand.

11. The functional prosthesis mechanism for a hand as claimed in claim 9, said support plate further comprising a light and non-corrosive material.

12. The functional prosthesis mechanism for a hand as claimed in claim 11, wherein said support plate is comprised of aluminum.

* * * * *